US00PP12120P2

(12) United States Plant Patent
Zary

(10) Patent No.: US PP12,120 P2
(45) Date of Patent: Oct. 2, 2001

(54) HYBRID TEA ROSE PLANT NAMED 'JACMEGA'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,224

(22) Filed: Dec. 6, 1999

(51) Int. Cl.[7] ..... A01H 5/00
(52) U.S. Cl. ..... Plt./134
(58) Field of Search ..... Plt./134

*Primary Examiner*—Howard J. Locker
(74) *Attorney, Agent, or Firm*—Klarquist Sparkman Campbell Leigh & Whinston, LLP

(57) ABSTRACT

A hybrid tea rose plant having bright yellow flowers on long stems; dark green, glossy foliage; resistance to rust and mildew; and vigorous, upright growth.

1 Drawing Sheet

The present invention relates to a new and distinct variety of rose plant of the hybrid tea class which was originated by me by crossing the variety JACyes (U.S. Plant Pat. No. 9,390), with an unnamed seedling.

The primary objective of this breeding was to produce a new rose variety having the bright yellow flower color, dark green foliage, resistance to disease and vigorous growth of the female parent, combined with the dark green, glossy, very disease resistant foliage and long stems of the male parent. The objective was substantially achieved, along with other desirable improvements, as evidenced by the following unique combination of characteristics that are outstanding in the new variety and that distinguish it from its parents, as well as from all other varieties of which I am aware:

1. Bright yellow, non-fading color of the flowers;
2. Dark green, glossy foliage;
3. Vigorous, upright growth;
4. Excellent dissease resistance; and
5. Long stems.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—JACyes (U.S. Plant Pat. No. 9,390).
*Pollen parent.*—Unnamed seedling.
Classification:
*Botanical.*—*Rosa hybrida.*
*Commercial.*—Hybrid tea.

FLOWER

Observations made from specimens grown in a garden environment at Somis, Calif. from March 1998 to August 1999.

Blooming habit: Continuous.
Bud:
*Size.*—About two inches long when the petals start to unfurl.
*Form.*—The bud form is long; pointed ovoid.
*Color.*—When sepals first divide, bud color is Yellow-Orange Group 15B. When half blown, the upper sides of the petals are Yellow-Orange Group 15C with some fading at petal margins to Yellow-Orange Group 15D; and the lower sides of the petals are Yellow-Orange Group 15C.
*Sepals.*—Color: Green Group 138B. Surface texture: Covered in fine hairs. There are three normally to heavily appendaged sepals. There are two unappendaged sepals with hairy edges.
*Receptacle.*—Color: Green Group 137B except when exposed to bright sun. Then they are Greyed-Purple Group 183B. Shape: Funnel. Size: Medium (about ¼ inch×5/32 inch). Surface: Smooth.
*Peduncle.*—Length: Medium (about three inches). Suface: Smooth. Color: Green Group 137B, but when in bright sun Greyed-Purple Group 183A. Strength: Stiff; heavy.
Bloom:
*Size.*—Large. Average open size is five inches.
*Borne.*—Singly.
*Stems.*—Strength: Strong. Average length is about 18 to 22 inches.
*Form.*—When first open: High centered. Permanence: Retains its form to the end; outer petals curl back.
*Petalage.*—Number of petals under normal conditions: 30.
*Color.*—The upper sides of the petals are Yellow-Orange Group 15C with some fading on petal margins to Yellow-Orange Group 15D. The reverse sides of the petals are Yellow-Orange Group 15C. The base of each petal has a small ⅛ inch×⅛ inch Yellow-Orange Group 17C half moon on both petal surfaces. The major color on the upper sides is Yellow-Orange Group 15C.
*Variegations.*—There are distinctive greenish-white streaks along the midrib of the guard petals.
*Discoloration.*—The general tonality at the end of the first day: No change. At the end of the third day: No change. By day six or seven, there is a general fading to Yellow-Orange Group 15D across most of the outer petal surface. By day eight there is general petal drop.

*Fragrance.*—Moderate; anise.

Petals:

*Texture.*—Thick.

*Shape.*—Round to deltoid.

*Form.*—Tips slightly recurved.

*Arrangement.*—Imbricated. No petaloids in the center.

*Persistence.*—Petals drop off cleanly before drying.

*Lastingness.*—On the plant: Long (about seven days). As a cut flower: Long (about eight or nine days).

Reproductive parts:

*Anthers.*—Size: Medium. Quantity: Many. Color: Yellow-Orange Group 20C. Arrangement: Regular around styles.

*Filaments.*—Color: Yellow-Orange Group 21C.

*Pollen.*—Present.

*Styles.*—Color: Green-White Group 157C.

*Stigmas.*—Color: Yellow-White Group 158D.

Plant:

*Form.*—Bush.

*Growth.*—Very vigorous; upright; branching. At maturity, height is six feet, width is 4½ feet.

Foliage: Number of leaflets on normal mid-stem leaves: five or seven.

*Size.*—Large (6 to 6½ inches long×4 to 4½ inches wide).

*Quantity.*—Abundant.

*Color.*—New foliage: Upper and lower surfaces: Greyed-Red Group 178A. Old foliage: Upper surface: Green Group 139A. Lower surface: Green Group 139B.

Leaflets:

*Shape.*—Pointed oval.

*Texture.*—Leather; glossy.

*Edge.*—Serrated.

*Serration.*—Single; small.

*Petiole rachis.*—Color: Green Group 137C. On young leaves, the upper surface is Greyed-Purple Group 187A.

*Petiole underside.*—Rough; with prickles.

*Stipules.*—Medium to long (about ¾ inch); serrated; bearded.

*Disease resistance.*—Resistant to mildew and rust, susceptible to blackspot under normal growing conditions.

Wood:

*New wood.*—Color: Greyed-Purple Group 187A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 187B.

*Color when mature.*—Greyed-Orange Group 177A.

Small prickles:

*Quantity.*—On main stalks: None. On laterals: None.

I claim:

1. A new and distinct variety of rose plant of the hybrid tea class, substantially as herein shown and described, characterized particularly by its bright yellow flowers on long stems; dark green, glossy foliage; resistance to rust and mildew; and vigorous, upright growth.

* * * * *

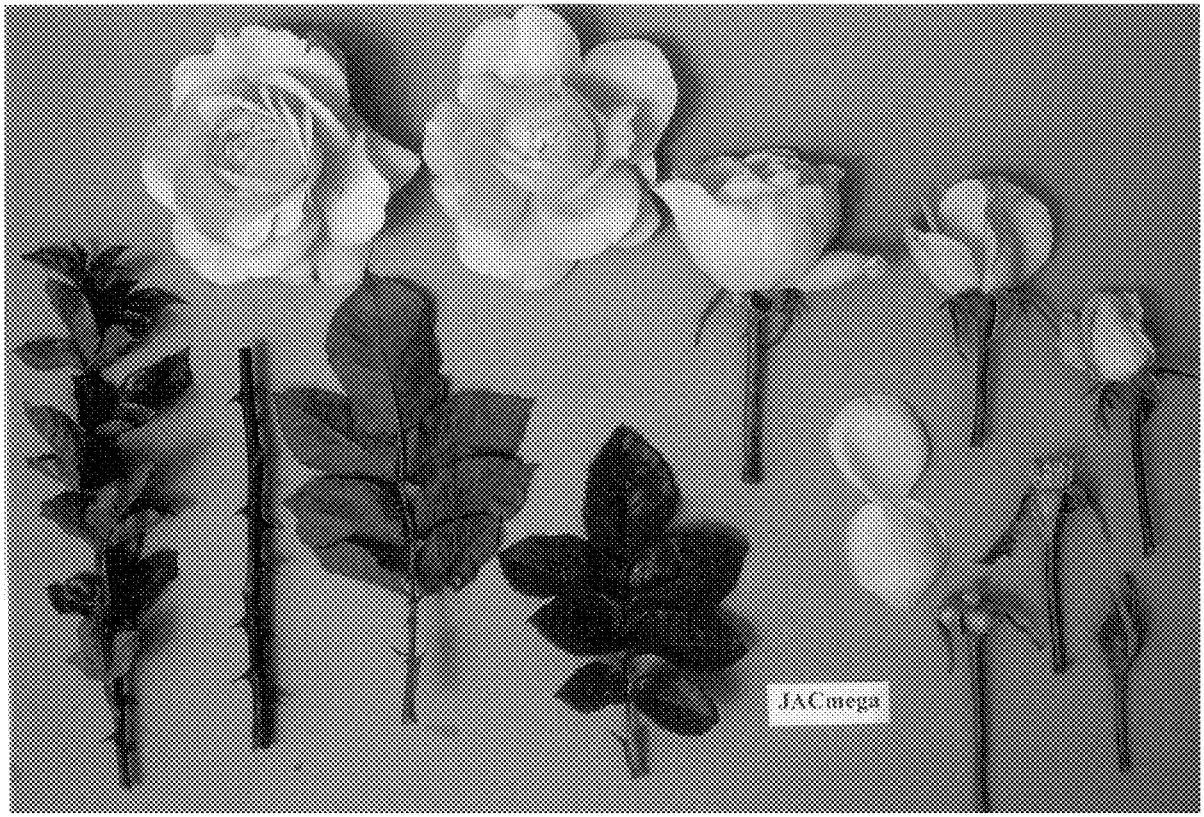
JAC mega